(12) United States Patent
McGee

(10) Patent No.: US 10,219,907 B2
(45) Date of Patent: Mar. 5, 2019

(54) DEVICES, SYSTEMS AND METHODS FOR ELONGATING BONE

(71) Applicant: Osteoceramics, Inc., Ames, IA (US)

(72) Inventor: Thomas D McGee, Ames, IA (US)

(73) Assignee: Osteoceramics, Inc., Ames, IA (US)

( * ) Notice: Subject to any disclaimer, the term of this patent is extended or adjusted under 35 U.S.C. 154(b) by 45 days.

(21) Appl. No.: 15/338,634

(22) Filed: Oct. 31, 2016

(65) Prior Publication Data

US 2017/0042681 A1 Feb. 16, 2017

Related U.S. Application Data

(60) Continuation of application No. 14/687,528, filed on Apr. 15, 2015, now Pat. No. 9,561,108, which is a division of application No. 14/205,494, filed on Mar. 12, 2014, now Pat. No. 9,039,781.

(60) Provisional application No. 61/787,985, filed on Mar. 15, 2013.

(51) Int. Cl.
*A61F 2/28* (2006.01)
*A61F 2/78* (2006.01)
*A61F 2/30* (2006.01)

(52) U.S. Cl.
CPC .............. *A61F 2/2814* (2013.01); *A61F 2/28* (2013.01); *A61F 2002/286* (2013.01); *A61F 2002/2817* (2013.01); *A61F 2002/2825* (2013.01); *A61F 2002/3082* (2013.01); *A61F 2002/30772* (2013.01); *A61F 2002/7887* (2013.01); *A61F 2250/0065* (2013.01)

(58) Field of Classification Search
CPC . A61F 2/2814; A61F 2002/7887; A61B 17/68
See application file for complete search history.

(56) References Cited

U.S. PATENT DOCUMENTS

2009/0182336 A1 * 7/2009 Brenzel .............. A61B 17/7225
606/62

* cited by examiner

*Primary Examiner* — Brian A Dukert
(74) *Attorney, Agent, or Firm* — Nyemaster Goode, PC

(57) ABSTRACT

The present invention comprises devices, systems, and methods for elongating bone using an extension implant having a first end and a second end. The first end of the extension implant is inserted into an opening in the live bone and the second end of the extension implant is combined with an enlarged implant. A plurality of channels extend through the components to serve as conduits for delivering fluids and physiological signals which induce bone formation. Some embodiments include a subcutaneous cage assembly for helping to support the implant as the bone heals around it.

18 Claims, 8 Drawing Sheets

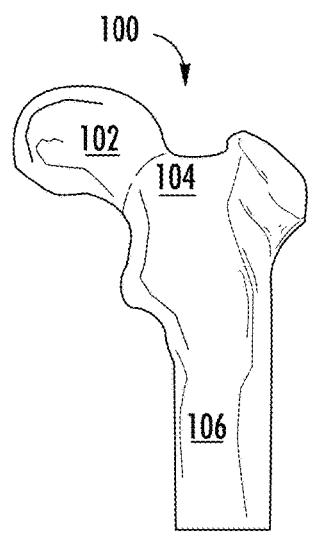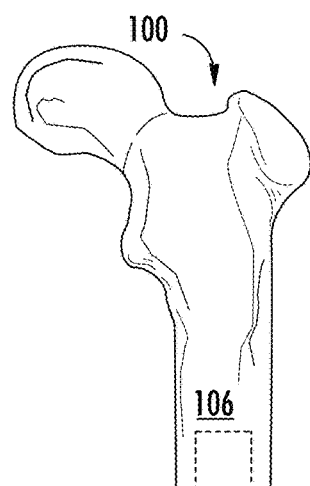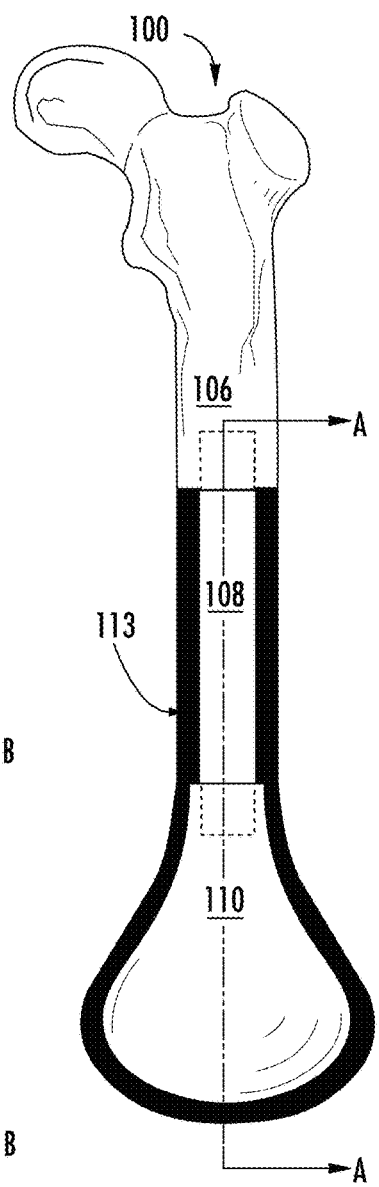
FIG. 1A
FIG. 1B
FIG. 1C

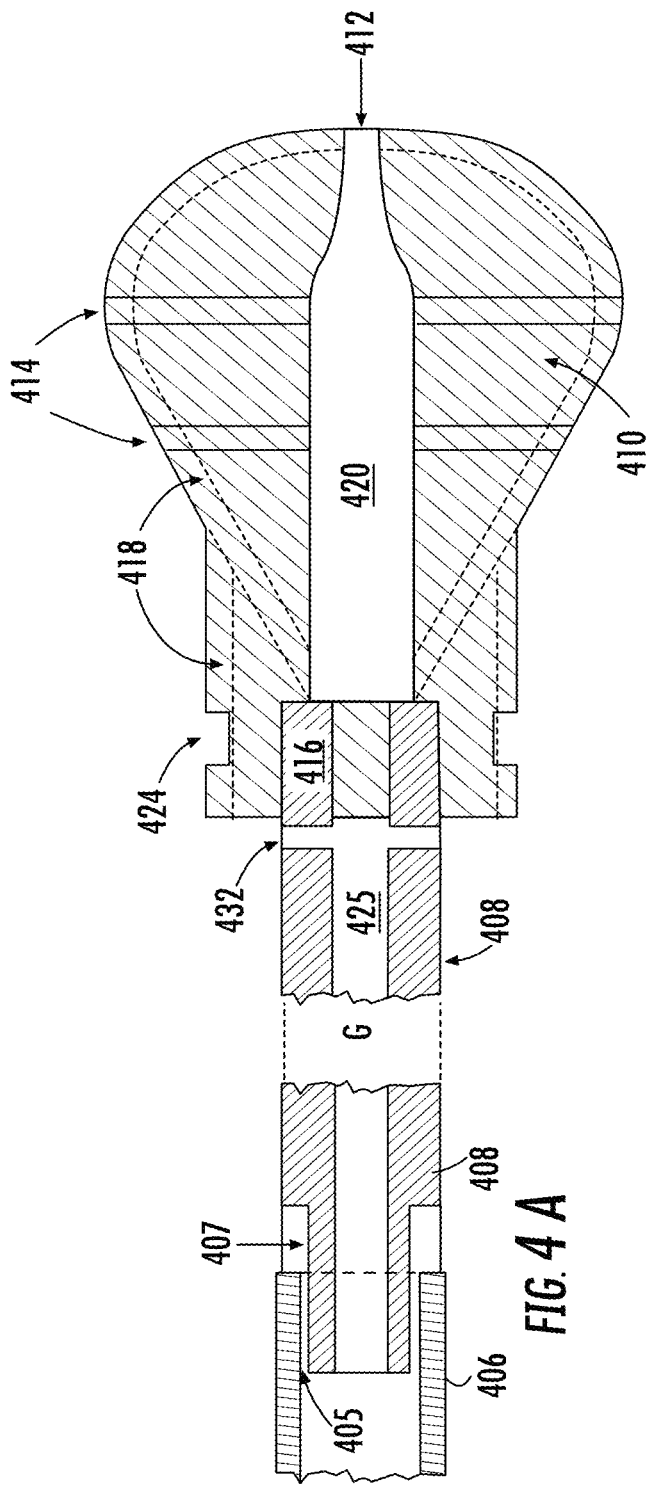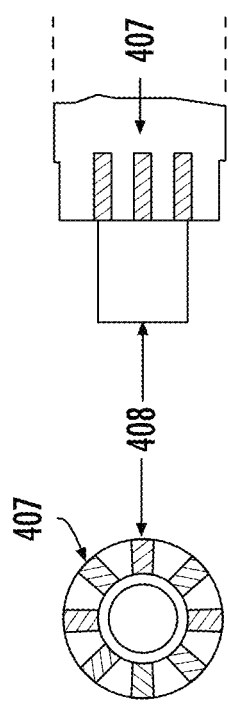
FIG. 4A
FIG. 4B
FIG. 4C

DEVICES, SYSTEMS AND METHODS FOR ELONGATING BONE

This application is a continuation of U.S. patent application Ser. No. 14/687,528 filed on Apr. 15, 2015 which is a divisional of U.S. Pat. No. 9,039,781 issued May 26, 2015 which is based upon U.S. Provisional Application No. 61/787,985 filed Mar. 15, 2013, the complete disclosures of which are hereby expressly incorporated by this reference.

BACKGROUND

Disease or injury often requires amputation of a portion of a limb. If the remaining bone is too short for prosthesis attachment, the patient has serious problems with the functions dependent on the missing portion of the patient's body. Often this harms lifestyle and causes deterioration of bodily functions that diminish longevity and have undesirable emotional and mental health consequences. Especially difficult are injuries to military personnel caused by improvised explosive devices. There is an urgent need for surgical devices and methods to help these severely disabled amputees.

Every patient has a unique situation. If the remaining portion of the limb can be elongated and provided with a functional structure for prosthesis attachment, the patient's prospects will be greatly improved. There is an urgent need for a device and method to elongate bone and to provide for prosthesis attachment.

Liver and bone are the only two organs of the human body that can regenerate after a loss of a part of the organ. Bone only regenerates when the loss is small, as in a simple fracture. About ten weeks is required to regain complete strength. For a larger defect from trauma or surgery, the surgeon may make the judgment that the bone will not regenerate even if it is held immobile in the proper position. In a fracture situation bone regenerates from both the proximal and distal bone fragments. A typical non-union results in closing at both ends with a somewhat hemispherical shape, with no bone in the gap between the fragments. This is true because the bone starts to regenerate from both ends of the defect until it rounds off with a hemispherical end before closing the gap, and no further regeneration will take place thereafter. When this is expected the surgeon must use a bone graft taken from the patient (autograft) or from the same species (allograft), usually a cadaver. These repairs take longer to heal and harvesting the bone for an autograft is a secondary surgery which is painful and increases the risk of infection and weakness at the harvest site. Because regeneration starts at both ends of the bone and because there is a limit at both ends for regenerating bone to grow, amputated bone has never been elongated. The bone end becomes rounded but elongation heretofore has not been possible.

The bone regeneration process is very complex and many factors affect regeneration with or without attempting to elongate it. An autograft is impractical when the harvested bone creates a similar defect, so some kind of artificial bone is needed. The challenge for elongating bone is to induce new bone to form at the distal end of the elongation so it can be a source of regeneration of connecting bone from both the proximal and distal ends and to prevent rounding off. The natural repair of a small loss of bone starts with a massive hematoma from capillaries and larger blood vessels. This produces a huge clot that quickly forms a fibrous scaffold when fibrinogen from the blood becomes a fibrous network. Once the network becomes strong, it is called a callus. For major injuries, several stages occur that take weeks or years to become dense, loading-bearing bone.

Stem cells for bone formation and for soft tissue formation appear from blood vessel walls and from pluripotent mesenchymal sources that are found in the waxy marrow of the long bones of the extremities, the sternum and the ilium. The delivery of the signals that stimulate the mesenchymal cells to produce the stem cells needed at a particular stage of regeneration is through systemic routes, such as the vascular system. The present state-of-the-art is based on harvesting a particular cell culture (only one of many that are needed), culturing it to multiply to high concentration, seeding a bone-like scaffold with high surface area and where further multiplication can take place, inoculating the scaffold/culture with growth factors, cytokines or bone morphogenic protein to increase multiplication rate, placing it surgically in a bone defect, and waiting for strong bone recovery. This method does not regenerate strong bone and has not been successful, but the description above shows how difficult it is. Note that the locations of mesenchymal cells are in places where they are protected from physical and chemical trauma and are surrounded by strong, protective bone.

Despite the worldwide efforts to make artificial bone, study stem cells, biomaterials, growth factors, antibiotics, etc. the basic sciences have not solved the problem of extension of amputated bone. Most of the efforts to make an artificial bone graft have depended on calcium phosphate and bioglasses as a tissue contact material or on tissue engineering to produce a graft that will be dissolved by tissue responses at the same rate as bone in rebuilding. Calcium phosphates and bioglasses, as possible bone graft substitutes, have been studied for over fifty years because they are not walled off by a foreign body response which invokes a fibrous capsule. All existing load-bearing materials used in current orthopedic practice are walled off, so the bone does not bond to them. The implants must be anchored in place by mechanical or geometric means, such as screws, beaded surfaces and cements (only PMMA cement is used for load-bearing applications. It has such undesirable tissue contact problems that it is used only if there is no other alternative.) Calcium phosphates and bioglasses are classical brittle materials that fail in tension when a local tensile stress at a flaw exceeds the fracture stress. Their bioactivity causes flaws to appear at tensile load locations making them completely unsuitable for load-bearing bone graft applications.

Tissue engineering has been studied for more than thirty years without achieving a successful load-bearing bone graft. The concept is based on three components: 1) cultured cells, such as a patient's osteoblasts, 2) a high surface area calcium phosphate scaffold on which the osteoblasts will grow in vitro and 3) growth factors to enhance the kinetics of cell growth and bone formation. The expectation that load-bearing bone will form on porous, weak, brittle, calcium phosphate scaffolds at the same rate the scaffolds are being resorbed is unjustified. The theory neglects the reality that the scaffold is too weak to support load even after bone is formed throughout because it will be disorganized chondroidal bone with very little strength. It also ignores the reality that the rate and character of bone formation depend on many factors, including applied load and the rate of scaffold resorption within the scaffold relative to the rate of scaffold resorption at the load-bearing bone/dense-bone interface. It would be very difficult for the rate of absorption to be adjusted to the rate of formation. What is needed is a permanent, bioactive strong, load-bearing implant.

The concept of a ceramic/ceramic composite was disclosed by McGee in U.S. Pat. No. 3,787,900. The first mineral in this composite is tricalcium phosphate which helps control tissue response and to prevent formation of a foreign body capsule. The second mineral in this composite is magnesium aluminate spinel, an inert biocompatible ceramic that gives the implant enduring strength. OSTEOCERAMIC is a brand of biologically active load bearing materials such as the one disclosed in McGee's Pat. No. 3,787,900.

The artificial OSTEOCERAMIC bone technology was modified in three later patents by McGee (U.S. Pat. Nos. 6,312,467, 6,364,909, and 6,719,793), through improved processing and sintering so that the external geometry could be utilized to guide bone generation and to which bone will bond. The implant became a "smart" implant (a "smart" material is one that repairs itself). The implant releases tricalcium phosphate at the crack surface and the local loss of strength induces adjacent bone to repair the implant/bone assembly to allow it to remain functional. The biologically active load bearing implant disclosed in U.S. Pat. No. 6,312,467 is the only load-bearing implant experimentally demonstrated to serve as a load-bearing artificial bone graft with only bone bonding to it to keep it functional.

A biologically active cement material was disclosed by McGee and Roemhildt in U.S. Pat. No. 6,723,334. This cement contains tricalcium phosphate to control tissue response and calcium aluminate as a hydraulic cement to cause the cement to set during surgery and to provide enduring strength. It is also a ceramic/ceramic composite sold under the OSTEOCERAMIC brand and is a smart material to which bone will bond.

Wolff's law states that bone remodels to support dynamic loads. The structure and strength of bone responds to loads. Skeletal loads are dynamic and experiments have shown that the remodeling to support load is faster and stronger if the load is dynamic. The dynamic load can be provided through physical therapy. When there is no load, regeneration produces weak non-load-bearing bone. Direct, load-bearing bone is only formed when the new bone has dynamic loading.

When a fracture occurs and bone is displaced it is necessary to reduce the fracture by realigning the displaced bone to its proper position and holding it in place until the bone regenerates. If the device holding it in place is insufficient, too much movement will occur and the newly forming repair bone will be destroyed. That movement is identified as macromotion and the amount of movement is called macrostrain. When the implants are put in place they must be held firmly enough in the correct position to avoid macromotion and the devices stabilizing them must be strong and rigid enough to prevent macromotion and macrostrain. For severe fractures the methods of holding them in place are usually internal and may include fastening a metal plate to the proximal and distal bone with the fracture reduced using bone screws as fasteners. Other means for securing such fractures is to use external fixation, where screws or wires are placed in the proximal and distal bone and an external cage is built around the limb so that the screws or wires hold the bones in their proper position. This requires a static (unchanging) load to be applied to the bone by the fixation devices.

SUMMARY

Objects of the present invention include one or more of providing devices, systems, and methods for elongating bone using an implant assembly which prevents a large external hematoma from forming, smearing the patient's stem cells on the surfaces where new bone is to be formed, inducing bone to form at the distal end of the implant assembly, providing a conduit that supplies blood to the geometrical shape (grooves, tubes, and openings) of the implant assembly, providing for physiological signals from the distal end to the live bone at the proximal end that supplies responses to those signals from the live bone back to the distal end, inducing new bone to form as dense load-bearing bone, guiding the bone to encapsulate the implant assembly, preventing fatigue failure, supporting the implant assembly as the new bone is formed until it is load-bearing, and/or providing for comfort in attaching a prosthesis.

It is a further object of the present invention to provide a strong biocompatible material for manufacturing the implant assembly for bone generation. In one embodiment the strong biocompatible material is a ceramic/ceramic composite comprising calcium phosphate and magnesium aluminate. In one embodiment the implant assembly has an elongated proximal extension and an enlarged distal end to distribute the stresses when a prosthesis is attached. Openings and conduits in the assembly allow the blood and physiological components to provide for controlled bone generation. Details of conduit construction, concepts and applications are disclosed in more depth in U.S. patent application Ser. No. 13/803,606 filed Mar. 14, 2013 which is hereby incorporated by reference.

It is a further object of the present invention to provide an implant assembly having an extension implant combined with an enlarged implant, wherein the extension implant comprises an open end extending into the live bone to be lengthened. In one embodiment the extension implant includes an internal conduit extending from its first end to its second end to allow for the passage of fluids therethrough. In one embodiment the conduit serves as a passage for the blood released at the live bone to fill the internal portions of the implant assembly and to reach openings and grooves in the implant assembly used to guide strong bone to encapsulate the implant assembly. In one embodiment the conduit serves as a passageway from the homeopoietic stem cell sources in the live bone to create a vascular system for new bone growth. In one embodiment the conduit serves as a pathway for physiological signals to connect directly with a source of pluripotent mesenchymal cells. In one embodiment the conduit serves as a pathway for the various stem cell responses to the source of the physiological signals to supply the many requirements for new cells as the new bone is formed.

It is a further object of the present invention to provide a fixation assembly for supporting the implant assembly and preventing macro-motion which may destroy new bone. In one embodiment the fixation assembly provides an adjustable static load to maintain the fixation assembly in place and to induce load-bearing new bone. In one embodiment provision is made for physical therapy to provide dynamic loads to induce load-bearing new bone.

In one embodiment the extension implant and the enlarged implant can be cemented to become a single unit. In one embodiment the extension implant and enlarged implant are manufactured as a single unit. In one embodiment the cement used to join the sections can comprise calcium phosphate and calcium aluminate. In one embodiment marrow is smeared on the accessible inner and outer surfaces of the implant assembly to enhance rapid generation of new bone. In one embodiment, the implant is fixed in place with a provision for load transfer.

The present invention comprises devices, systems, and methods for elongating bone using an implant assembly having an extension implant combined with an enlarged implant. The extension implant has a first end and a second end combined by an internal conduit. The enlarged implant comprises a first end and a second end combined by an internal conduit. The second end of the extension implant is adapted to combine with the first end of the enlarged implant thereby allowing fluids to flow between the two implant components. Various openings, holes, grooves or channels are included in the extension implant and the enlarged implant to allow fluids to flow from the internal conduits to the outer surfaces of the respective implants. In use, the first end of the extension implant is inserted or immersed into an opening in the live bone and the second end of the extension implant is combined with the enlarged implant to produce an implant assembly with internal fluid passageways from the live bone throughout the implant assembly. The conduits, openings, and grooves make a direct fluid connection between the living tissue generation components and all parts of the assembly where guided bone generation is to take place. Physiological signals from the new bone generation site have a direct fluid connection to the source of mesenchymal or hematopoietic cells in the bone to stimulate them to produce stem cells to deliver the needed cells to the new bone generation sites. The physiological signals are many and may include blood pressure, electrical potential, growth factors, oxygen pressure and physical stress. The enlarged implant is adapted to accommodate a prosthesis and to distribute the load at the end of the limb in contact with the prosthesis. The enlarged implant elongates the bone by inducing the bone to bond with and encapsulate it to prevent fatigue failure. The new bone formed on the enlarged implant becomes a functional part of the limb and may be combined with a prosthetic limb. Provision is included to elongate the end of the bone in contact with the prosthesis where necessary.

Every bone elongation surgery is unique. The orothopaedic implants must be designed to fit the patient's needs. This is very difficult because the fixation assembly must carry the whole of the load immediately after surgery and support the implant assembly without fracturing it, but the load must be gradually transferred to the bone-implant assembly until the fixation can be removed at the end of the regeneration period. One embodiment of the present invention includes a subcutaneous fixation device for controlling the loading sequence as the bone is healed.

BRIEF DESCRIPTION OF THE DRAWINGS

FIG. 1A is a front view of a left femur viewed anterior-posterior (AP);

FIG. 1B shows the femur of FIG. 1A with a tubular extension implant and an enlarged implant after bone lengthening surgery;

FIG. 1C shows the femur of FIG. 1B after some time has passed to allow cortical bone to encompass the implants;

FIG. 4A is a side section view taken along lines A-A of FIG. 1 showing the implant assembly combined with the distal end of the femur;

FIG. 4B is an end view illustrating the proximal end of the extension implant;

FIG. 4C is a side view of the proximal end of the extension implant;

DETAILED DESCRIPTION

Figure 2:
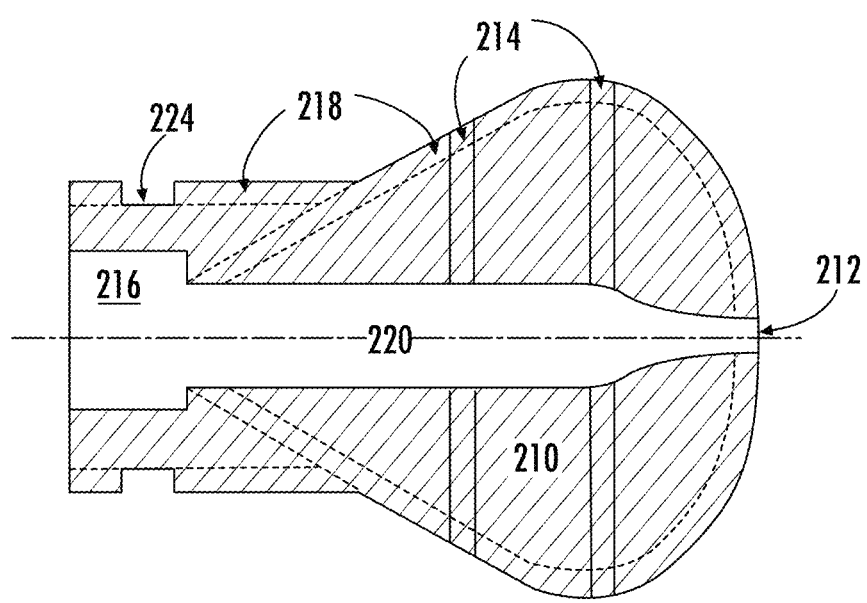
FIG. 2 is a section view taken along B-B of FIG. 1B showing details the enlarged implant.

Devices, systems and methods for elongation of bone are described herein using a short femur model, not as a limitation but as a mechanism for explanation. The present invention can be applied to all kinds of bones and surgical situations.

The accompanying figures are used to display the features of the present invention. Features are identified by an identification method whereby the first number of a three letter sequence designates the figure number. The second two digits designate the particular feature of the bone or implant that is of interest. That same feature will have the same two digit number in all subsequent figures. For example, element 110 in the first figure will be the same as element 310 in the third figure. Further, it should be noted that "distal end" is used herein to describe elements or portions of elements which are farther from the hip joint 102 and "proximal end" is used herein to describe elements or portions of elements which are closer to the hip joint 102.

The present invention comprises devices, systems, and methods for elongating bone using an implant assembly having an extension implant 108 combined with an enlarged implant 110. Taken in succession, FIGS. 1A, 1B, and 1C show a simplified overview of the implant assembly and a process for using the implant assembly with a short femur bone 100. The figures show a bone 100, the extension implant 108, and the enlarged implant 110. The extension implant 108 has a first (proximal) end and a second (distal) end combined by a conduit 425 (not shown in FIGS. 1A, 1B, and 1C) which allows fluids and physiological signals to flow between the two ends. The enlarged implant 110 is combined with the second end of the extension implant 108 as further described below. The implants 108, 110 may be comprised of any suitable bone graft composition, including OSTEOCERAMIC material. In one embodiment, the composition of the implants 108, 110 stimulates bone formation because it comprises tricalcium phosphate which dissolves more rapidly than bone mineral (hydroxyapatite), produces a high pH, and serves as a reservoir for calcium phosphate to induce bone formation.

FIG. 1A shows three features of a left femur 100 viewed anterior-posterior (AP) or looking from the front. The ball of the femur 100 in the hip joint is reference number 102. The stem connecting it to the femur 100 is reference number 104 and the shaft of the bone remaining after amputation is reference number 106. In this example, not much of the shaft 106 remains.

FIG. 1B shows the result after bone lengthening surgery wherein the extension implant 108 and enlarged implant 110 have been combined with the bone 100. The distal end of the remaining femur bone 106 has been removed and an opening has been made therein to allow the extension implant 108 to fit into the femur's shaft 106 with enough annular space between the cortical bone of shaft 106 and the external end of extension implant 108 to allow for fluid exchange between the inside of the opening in femur bone 106 and the external proximal end of extension implant 106; and to allow fluid exchange between the inside opening of bone 106 and the conduit 425 inside the extension implant 108.

There is a separate vascular system for the marrow cavity (not shown). In use, the proximal end of the extension implant 108 is immersed in the marrow cavity of bone's shaft 106 to allow the homeopoietic stem cells and mesenchymal cells to be in fluid communication with the extension implant 108. The extension implant 108 provides structural support for the enlarged implant 110. It also provides a direct pathway (through conduit 425) for physiological signals between its second end (distal) end (adjacent to enlarged implant 110) and its first (proximal) end (adjacent to bone 100). The extension implant 108 also provides a direct return pathway for the responses of the homeopoietic stem cells to form a vascular system within the extension implant 108, and also provides a direct pathway for the responses from the mesenchymal cells to induce the wound healing, soft tissue, and bone processes necessary to generate new strong, load-bearing bone that will bond to both implants 108, 110 and encapsulate them.

Long bones, including femurs, have nearly tubular shape and have two blood-carrying membranes to nourish the walls of the bone—the periosteum on the external surface and the endostium on the interior surface. Each has a vascular system with longitudinal orientation and each supplies cells (osteoclasts) for breaking down bone and cells for building bone (osteoblasts). FIG. 1C shows the desired result after healing wherein strong new cortical bone 113 encompassing the implants 108 and 110 has formed. The dark line of the new bone 113 shows the thickness of the layer around the implants for clarity but does not show the encapsulation on the surfaces of implants 108 and 110 that are facing the reader. FIGS. 1A-1C do not show all of the details of the implants 108, 110 but do show the desired result of encapsulated implants 108, 110 to which the bone will bond so that the mature bone/implant assembly will be functionally strong and fatigue resistant. The length of the extension implant 108 in FIG. 1C is shown to represent an exemplary length that could be possible if flesh and soft tissue can accommodate it. Extension implant 108 can be shortened to the point that the implant 110 is touching the bone's shaft 106, if necessary. These dimensions are to explain the principles involved and are not to be taken as limiting for various other patient bones and implants.

FIG. 2 shows an embodiment of the enlarged implant 210. It is a sectional view so that the internal components can be seen easily. The enlarged implant 210 comprises a seat 216 adapted to receive the distal end of extension implant 108 (not shown in FIG. 2). As mentioned above with respect to the proximal end of the extension implant 108 in relation to the bone 100, in one embodiment the extension implant 108 fits into seat 216 such that there is space between the outside diameter of the extension implant 108 and the inside diameter of the seat 216. Bone cement can be used to fill the space and bind the implants 108, 210 together so the surgeon can handle the assembly as one unit during surgery. When the implants 108, 210 are connected, the conduit 220 is contiguous with the conduit 425 of extension implant 108 (not shown in FIG. 2) thereby making a direct conduit connection between the two implants 108, 210.

FIG. 2 shows an embodiment wherein the enlarged implant 210 has a larger diameter than the extension implant 208. The larger diameter provides additional strength which may be necessary if the enlarged implant 210 is combined with a prosthetic limb. Further, the larger diameter provides a greater surface area for the prosthetic limb to attach and for new bone to attach and grow.

As shown in FIG. 2, the enlarged implant 210 may include exterior grooves 218 and radial openings 214 connected to the conduit 220. Together, the grooves, 218, openings 214, and conduit 220 direct fluid flow through the enlarged implant 210 to help guide bone formation. The grooves 218 are in the outer surface of the enlarged implant 210 and are adapted to capture fluids traveling from the live bone 100 and to induce new bone formation. The new bone eventually encapsulates the entire implant assembly 210 as shown in FIG. 1C. The radial openings 214 are fluidly combined with the grooves 218 and provide fluid conduit pathways between the grooves 218 and the internal conduit 220. FIG. 2 also shows an embodiment having an axial opening 212 in the distal end of the enlarged implant 210 to allow additional fluid access to the grooves 218 which stimulates bone regeneration and allows an axial wire or rod 840 to be used as part of the stabilization system which is described later with referenced to FIG. 8.

Strong bone only attaches to an implant if it has dynamic microstrain to stimulate direct formation of cortical bone. If no dynamic loading to create the microstrain is applied, then the new bone, if any, will not be strong. Therefore, the implant assembly must be fixed in position to only allow microstrain. As shown in FIG. 2, one embodiment includes a groove or depression 224 in the outer surface of the enlarged implant 210. The depression 224 is adapted to allow a support band 830 to be fastened tightly to the implant assembly for stabilization (described below with referenced to FIG. 8). This can be done before surgery begins.

Figure 3:
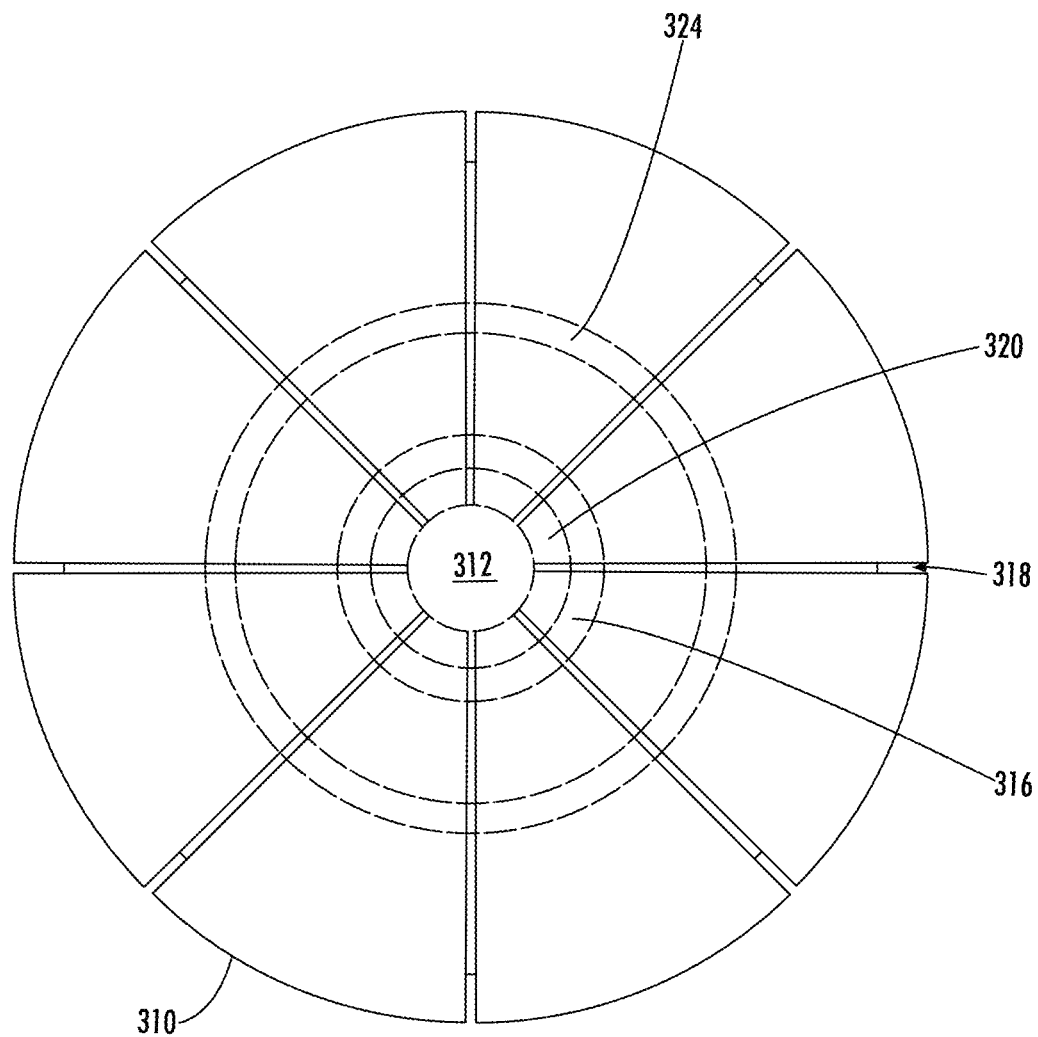
FIG. 3 is a distal end view of the enlarged implant.

FIG. 3 is an end view showing additional detail of an embodiment of the enlarged implant 310. Specifically, FIG. 3 shows the geometries and various relative diameters of the components described above and the placement of the longitudinal grooves 318 with reference to FIG. 2. FIG. 3 shows the surface of the enlarged implant 310 is rough with a plurality of grooves 318 and openings 312 therein. The rough surface helps to induce new bone formation. The axial opening 312 has the smallest diameter and connects to the axial grooves 318 for guided bone regeneration to promote encapsulation of the entire implant 310. The radial openings 214 also connect to enlarged implant conduit 320, but they are not visible when viewed from the distal end because the dashed lines of radial openings 214 are overlapped by the solid lines of the axial grooves 318. The relative diameters of the seat 316 and depression 324 are also shown.

FIG. 4A is a detailed cross section of the extension implant 408 combined with the enlarged implant 410. The proximal end of the extension implant 408 is combined with the distal end of the femur shaft 406. In one embodiment the extension implant 408 is secured firmly against the ends of the cortical bone (tube wall) of bone 406 (fixture not shown). The annular space 405 connects with the openings 407 (also shown in FIGS. 4B and 4C) in extension implant 408 to make a conduit for blood flow, bone generation, and bone encapsulation around the proximal end of extension implant 408. While most of the fluids will flow from the live bone 100 into the conduit 425 of the extension implant 408, the annular space 405 allows a small amount of fluids to flow around the outside of the extension implant 408 and through openings 407 to induce new bone formation around the outer surface of the implant assembly. The annular space 405 allows new bone 113 around the outside of the implant assembly to have a proximal blood supply as it regenerates to encapsulate the outside surfaces of the implants 408 and 410.

In an alternate embodiment, the extension implant 408 is firmly secured against the ends of the cortical bone (tube wall) of bone 406 (fixture not shown) such that no annular space 405 exists between the implant 408 and the bone 406. In this embodiment the extension implant 408 comprises one or more openings in its proximal end (similar to opening 432 in the distal end) which allows a small amount of fluids to flow around the outside of the proximal end of the extension implant 408 to induce new bone formation around the outer surface of the implant assembly.

As shown in FIG. 4A, some embodiments include an opening 432 near the distal end of the extension implant 408. The opening 432 serves a function similar to the openings 407 described above. The opening 432 allows fluids to flow from the conduit 425 to the outside of the implant assembly. The fluids allow new bone to form around the outside surfaces of the implants 408, 410 and eventually encapsulate the implants 408, 410. The opening 432 is small when compared to the diameter of the conduit 425 to force most fluids through the conduit 425 of the extension implant 108 and into the enlarged implant 410.

As discussed above, FIG. 4A shows the fluid connection between conduit 425 inside extension implant 408 and conduit 420 inside enlarged implant 410, which is fluidly combined with grooves and openings 414, 418 and 412. The fluid connection between these components induces bone regeneration and encapsulation of the implants 408, 410 since it allows fluids and signals to flow from the live bone shaft 106 to the distal end of the enlarged implant 410. The extension implant 408 is shown with a gap G in its center to illustrate that the length of the extension implant 408 can be varied to fit the patient's need.

The contact area between the distal bone shaft 406 and the proximal end of the extension implant 408 is drawn to show the clear path of blood flow for bone regeneration. FIG. 4B is an end view of the proximal end of extension implant 408 showing truncated triangles of the solid extension implant 408 which actually contact the bone 406 at the interface. The radial openings 407 that connect with the annular openings 405 between bone 406 and extension implant 408 are darkened for contrast purposes. FIG. 4C is a side view of the proximal end of the conduit 408 showing the length of the marrow extension and the length of the end of extension implant 408 that contacts proximal bone 406.

Direct Bone Formation

In some embodiments, direct bone formation requires strong, dense permanent bioactive implants, hematoma control, the availability of hematopoietic cells and mesenchymal cells, static load to provide stability, stabilization to prevent macrostrain, dynamic load to produce microstrain to stimulate strong bone formation, and to prevent fatigue failure. These features are discussed below.

Strong Dense Bioactive Implants

Permanent implants for load bearing applications such as bone grafts and the elongation of bones need to be bioactive so the bone will bond to them instead of walling them off with a fibrous capsule. Any suitable biologically active load bearing material may be used for the implants 108, 110 of the present invention, including OSTEOCERAMIC materials. In one embodiment the implants 108, 110 are made from a material comprising tricalcium phosphate to control tissue response. The tricalcium phosphate is more soluble than bone so it is a reservoir of calcium phosphate at the site for bone rebuilding. It also establishes a high pH which inhibits osteoclast resorbtion and promotes osteoblast formation of bone. This induces new dense bone to form and increases the rate of formation. In one embodiment the remaining component of the material comprises magnesium aluminate which contributes high strength. The compressive strength is as strong as dense bone. It can be readily machined to complex shapes which are beneficial for bone elongation.

Hematoma Control

Severed bones produce a flood of blood that is uncontained and produces a massive hematoma which becomes a large fibrous scaffold within a few hours. Ultimately, the periosteum forms on the outer surface of the hematoma and mineralization starts there (away from the original bone). The scaffold has an amazing amount of strength to help a fracture become stabilized. But it slowly converts to a chondroidal structure which slowly becomes mineralized new bone. Fracture healing typically takes about ten weeks to be load-bearing and two years to be remodeled.

Figure 5:
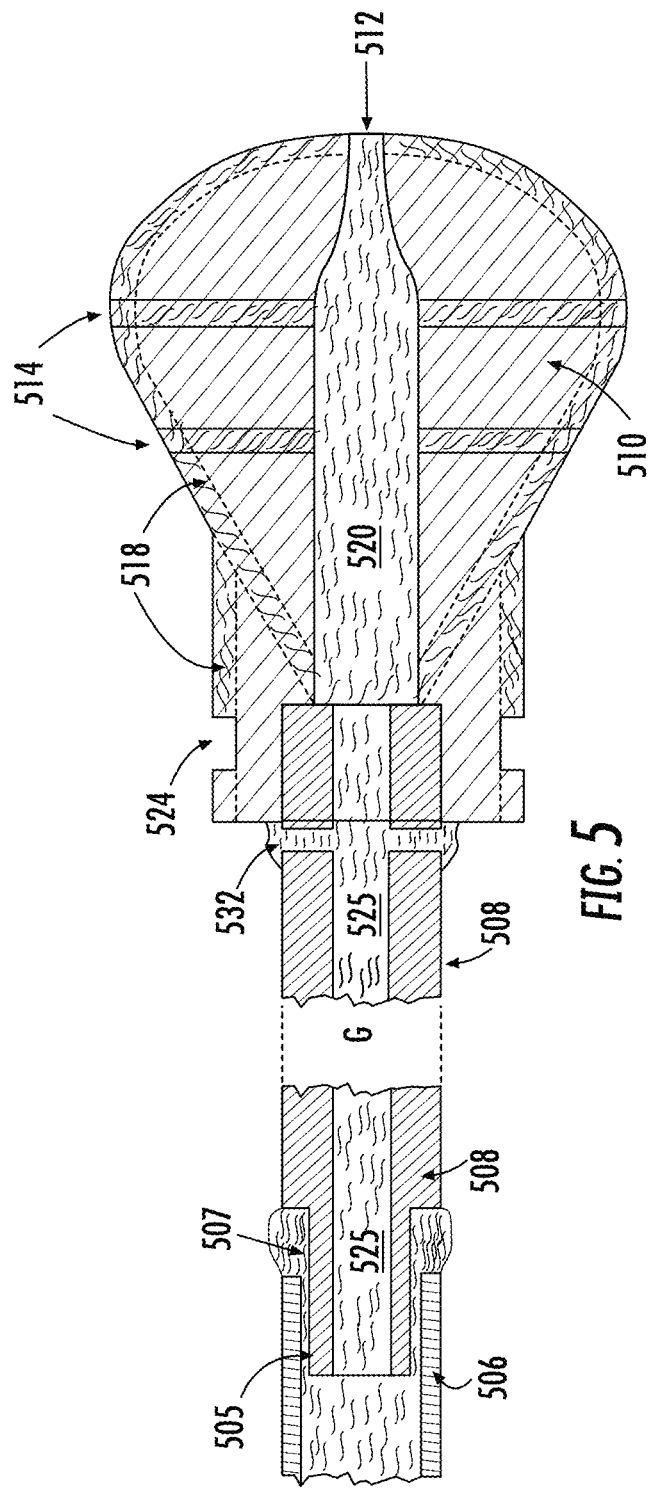
FIG. 5 is a side section view taken along lines A-A of FIG. 1 showing the implant assembly combined with the distal end of the femur with flow marks to represent the flow of blood through the conduit composed of the central cavity and all the internal and external passages for controlled bone regeneration.

The blood supply for bone regeneration must be provided and controlled to prevent the massive hematoma which produces chondroidal bone. FIG. 5 includes flow-lines to show how the flood of blood during surgery fills the conduit 525 within the extension implant 508, then conduit 520 within the enlarged implant 510, then finally the connecting channels, openings, and grooves 518, 514, 512, 532. FIG. 5 further shows how the blood flows through the annular space 505/opening 507 and through opening 532 to help encapsulate the outer surface of the implants 508, 510. In this process the delivery of blood to the places where new bone is needed induces rapid generation of new bone at the distal end in addition to the proximal end and guides bone generation to encapsulate the implants 508 and 510. The confined blood forms the desired localized hematoma that will develop into the vascular system needed for bone generation. The presence of the extension implant 508 prevents a massive external hematoma which would result in chondroidal bone formations and prevent elongation. For direct bone formation, the surgical placement of a strong permanent bone graft in contact with the bleeding area, so that the only leakage of blood at the proximal end takes place through the annular space 505 that is connected to openings 507 where a small external leakage is needed to form proximal encapsulating bone.

Availability of Mesenchymal Cells and Hematopoietic Cells

The extension implant 508 allows physiological signals from the surgical site to stimulate formation of mesenchymal and hematopoietic sources to respond to stimulus and proliferate bone formation entities to migrate directly to the surgical site much faster than the systemic processes normally available. The extension implant 508 function is continued in the enlarged implant 510 as the direct connection includes all of the geometric features needed to form new bone to encapsulate the entire implant assembly 508, 510. Stem cells, growth factors, cytokines, bone morphogenic proteins, sequences of processes and many complex factors are not completely understood. The direct connection, using the patient's own bone growth stimulants, is important. As new bone is formed the physiological signals from the formation site can migrate through the conduit to stimulate formation of stem cells from the mesenchymal cells in the marrow. Mesenchymal cells after puberty are found in waxy yellow bone marrow in protected locations such as in the diaphysis of long bones. Histological examination of tubular bone grafts using OSTEOCERAMIC material shows this marrow can be continuous from proximal to distal through the graft. At the time of surgery, it can be transferred from the patient bone.

In one embodiment, blood, hematopoietic cells and stem cells are harvested from the epiphysis when the extension implant 508 is inserted into the amputated bone and delivered to inner and outer surfaces of the extension implant 508 and the enlarged implant 510 at the time of surgery. In one embodiment, a marrow containing mesenchymal cells is spread onto the surfaces of implants 508, 510 to stimulate and enhance the rate of bone formation.

Figure 6:
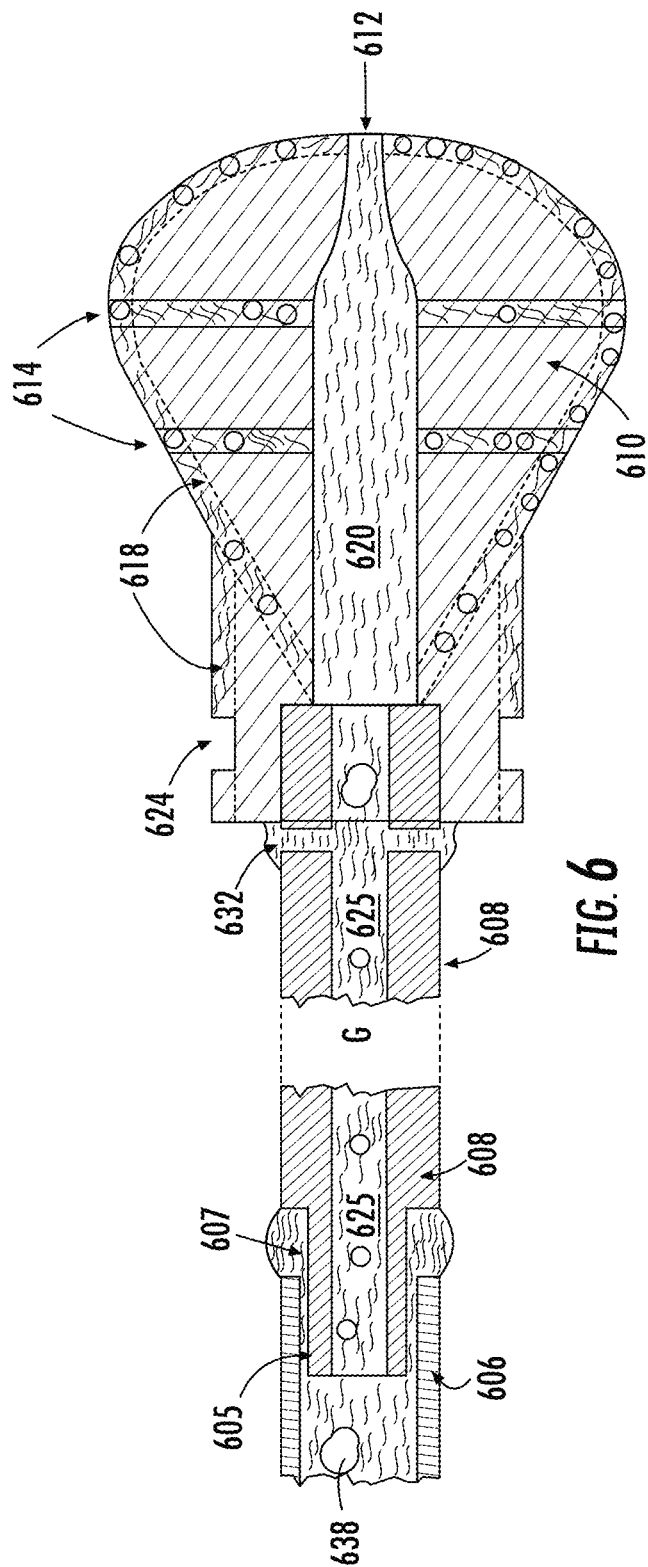
FIG. 6 is a side section view taken along lines A-A of FIG. 1 showing the implant assembly combined with the distal end of the femur showing the presence of the homeopoietic components distributed through the implant assembly and regeneration sites.

The epiphysis of long bone joints is filled with a rich supply of blood, hematopoietic stem cells and porous bone. FIG. 6 is a cross section showing the blood-filled implant assembly representing the presence of the homeopoietic components as white particles 638 distributed through the extension implant 608 to the enlarged implant 610 and to the smaller regeneration sites. This distribution enhances the development of the vascular system needed for new bone formation.

Figure 7:
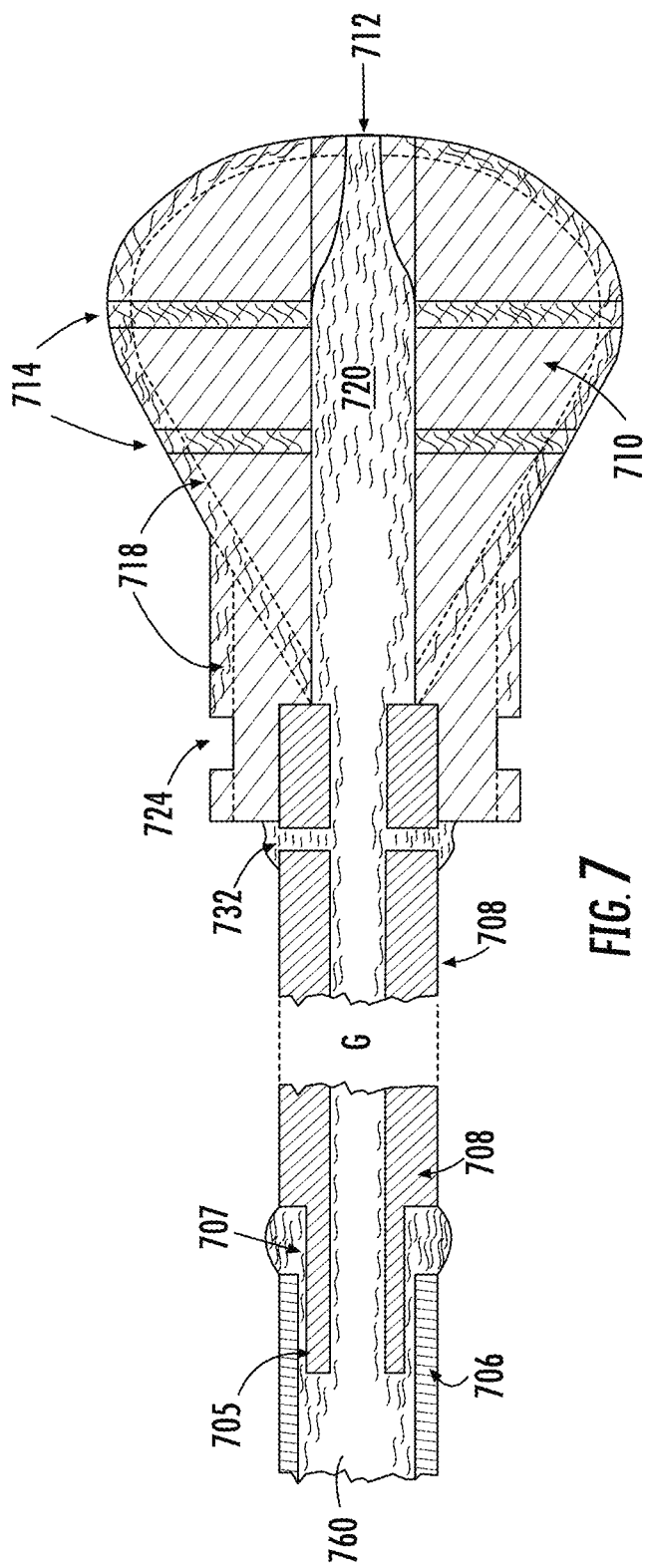
FIG. 7 is a side section view taken along lines A-A of FIG. 1 showing the implant assembly combined with the distal end of the femur showing the mesenchymal cells.

Mesenchymal cells may be available at the bone extension site from the diaphysis. If not, they can be harvested from the most practical site for the patient. This is a surgical judgment that is unique to the patient. It is preferable to harvest yellow, waxy bone marrow as an intact rod taken with a tubular cannula. This can be transferred to the extension implant 608, a protected site similar in physiological environment to the harvest site. FIG. 7 is a schematic of the blood-filled implant assembly showing the mesenchymal cells as a large white area 760 on the axis of the extension implant 708 and extending into distal bone shaft 706 and into enlarged implant 710.

Implant Stabilization, Static and Dynamic Loading

Elongating amputated bone is difficult because there is no distal bone. Therefore, some type of fixation is necessary to hold the implants 808, 810 in place and also provide some loading to the bone, which helps induce bone formation and bone strength. Any suitable fixation method can be used with the present invention, however, one embodiment includes a subcutaneous cage assembly which is disclosed below and shown in FIG. 8.

Figure 8:
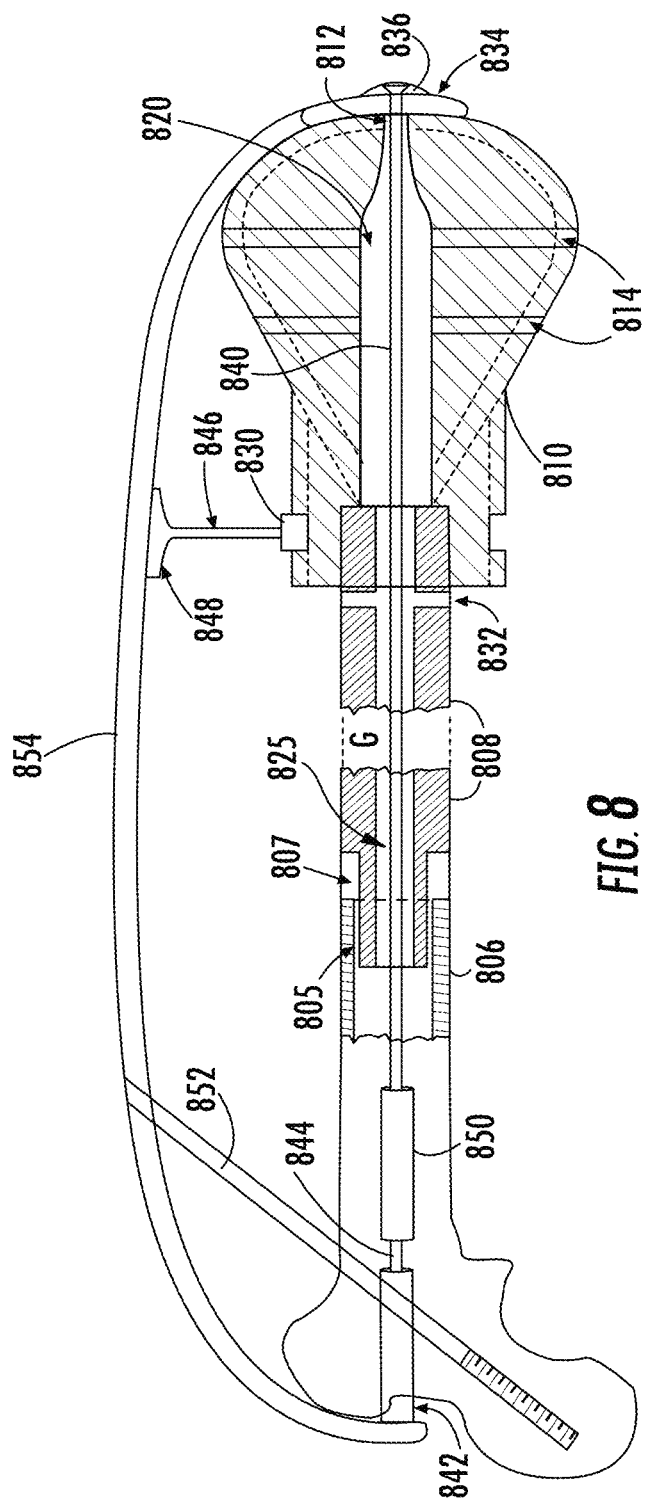
FIG. 8 is a side section view taken along lines A-A of FIG. 1 showing the implant assembly combined with the distal end of the femur showing an embodiment using a subcutaneous stabilization system.

As shown in FIG. 8, the subcutaneous cage assembly generally comprises an axial tension member 840 extending through the implant assembly and having a first end combined with the distal end of the enlarged implant 810 and a second end combined with the bone 100, an axial band 854 extending around the outside of the implant assembly and having a first end combined with the distal end of the enlarged implant 810 and a second end combined with the bone 100, and a stabilization band 830 adapted to be received by depression 224 in the enlarged implant 810 and combined with the axial band 854.

The axial tension member 840 may be a wire, rod, or other suitable connection member. It extends through the internal conduits 820, 825 of the implant assembly 808, 810 to combine with the distal end of the enlarged implant 810 at one end and the bone 100 at the other end. In this manner, the axial tension member 840 may apply compressive force between the implant assembly and the bone 100 by pulling the distal end of the implant assembly toward the bone 100 to help secure the implant assembly with the bone 100. The axial opening 812 in the enlarged implant 810 is adapted to receive one end of the axial tension member 840. The axial tension member 840 is combined with a tension member end cap 836 on the outside of axial opening 812. The tension member end cap 836 is supported by the distal end plate 834. These components 834, 836 are wider than the axial opening 812 and therefore remain outside the axial opening 812 under tension. A proximal anchor 842, 850 is combined with the bone 100 to provide a stable attachment point for the proximal end of the axial tension member 840. In one embodiment, the proximal anchor 842, 850 comprises an adjusting mechanism 844, such as an adjusting screw capable of changing the distance between the proximal anchors 842, 850 to adjust tension on the axial tension member 840 for the static force holding the implant assembly to the bone 100. In one embodiment the tension adjusting mechanism 844 can be built into the distal end of axial tension members 840.

The axial band 854 is made from a semi-rigid material and is adapted to help secure the implant assembly to the bone 100 by extending around the outside of the implant assembly. The axial band 854 has a first end combined with the distal end of the enlarged implant 810 and a second end combined with the bone 100. In one embodiment, the first end of the axial band 854 is combined with the end plate 834 and the second end of the axial band 854 is combined with the proximal anchor 842. This provides two secure points of attachment to help stabilize the implant assembly relative to the bone 100. In some embodiments, the axial band 854 may also be combined with proximal anchor 850 via stabilizing member 852. As describe above, proximal anchor 850 is movable relative to proximal anchor 842 thereby allowing the tension of axial band 854 to be adjusted through member 852 when the two proximal anchors 842, 850 are adjusted. In some embodiments, the stabilization band 830 provides another connection means between the implant assembly and the axial band 854. The stabilization band 830 is described below in more detail. These various connection means provide strong support to the entire implant assembly in addition to an adjustment mechanism to adjust static axial load. Additional anterior and/or posterior bands can be added but they may not connect to the screw pin 852. Also conventional external fixation can be added to strengthen and maintain position for a short time after surgery.

The stabilization band 830 is received in groove 424 and compresses the proximal end of enlarged implant 810 to minimize tensile failure and helps ensure the extension implant 808 is secured firmly in seat 216. The stabilization band 830 is combined with the axial band 854 by a connection assembly which may comprise a flattened and contoured subcutaneous stabilization band 848 connected through radial pins 846 to the stabilization band 830. This creates a hub-and-spoke like connection assembly where the stabilization band 830 is the hub and radial pins 846 are the spokes for connecting to the axial band 854. This provides a strong rigid support to the enlarged implant 810. Because of the large area of the band 848, external padding may be used to provide control for comfort. The geometries of the components shown in FIG. 8 are illustrative of principles and can be varied to fit surgical and patient requirements. They are not to be taken as limiting.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

I claim:

1. An implant assembly to enhance bone elongation comprising:
   an extension implant having a first end, a second end, an external surface, an interior conduit, and a diameter, wherein the first end is adapted to be inserted into live bone;
   an enlarged implant having an interior conduit, wherein the interior conduit of the extension implant is in fluid communication with the interior conduit of the enlarged implant, wherein the enlarged implant is combined with the second end of the extension implant, and wherein the enlarged implant has a diameter at one end that is larger than the diameter of the extension implant; and
   a plurality of grooves on an outer surface of the enlarged implant, the grooves in fluid communication with the interior conduit of the enlarged implant through openings, whereby the interior conduit is confining such that the only fluid being released from the interior conduit is through the openings.

2. The implant assembly of claim 1 wherein the interior conduit of the extension implant further comprises a sidewall, and wherein the extension implant has an opening in the sidewall to allow fluid to flow from the interior conduit of the extension implant to the external surface of the extension implant to control and guide bone formation around the enlarged implant.

3. The implant assembly of claim 1 further comprising a subcutaneous cage assembly having a first end combined with the enlarged implant and a second end adapted to be combined with the live bone, the subcutaneous cage assembly adapted to secure the extension implant and the enlarged implant to the amputated live bone.

4. The implant assembly of claim 1 wherein the extension implant and the enlarged implant are comprised of calcium phosphate.

5. The implant assembly of claim 1 wherein the extension implant and enlarged implant are made of a biologically active load bearing material.

6. The implant assembly of claim 1 wherein the extension implant and enlarged implant are combined thereby making a single assembly.

7. An implant assembly to enhance bone elongation comprising:
   an extension implant having a first end, a second end, an external surface, an interior conduit, and a diameter, wherein the first end is adapted to be inserted into live bone;
   an enlarged implant having an interior conduit and a rough surface with a plurality of openings in communication with the interior conduit, wherein the interior conduit of the extension implant is in fluid communication with the interior conduit of the enlarged implant, wherein the enlarged implant has a first end combined with the second end of the extension implant and a second end having a diameter that is larger than a diameter the first end of the enlarged implant and larger than the diameter of the extension implant, whereby the interior conduit is confining to prevent fluid from leaking outside of the interior conduit except through the openings.

8. The assembly of claim 7 wherein the openings in the rough surface of the enlarged implant are in fluid communication with the interior conduit of the enlarged implant, and further providing that fluid flows to the outside of the interior conduit through the openings.

9. The assembly of claim 7 having an axial adjustable tension member adapted to be attached to an existing bone with a proximal anchor on one end and attached to the enlarged implant with a cap on another end.

10. The implant assembly of claim 7 further comprising a subcutaneous cage assembly having a first end combined with the enlarged implant and a second end adapted to be combined with the live bone, the subcutaneous cage assembly adapted to secure the extension implant and the enlarged implant to the amputated live bone.

11. The implant assembly of claim 7 wherein the extension implant and enlarged implant are made of a biologically active load bearing material.

12. The implant assembly of claim 7 wherein the extension implant and enlarged implant are combined thereby making a single assembly.

13. The assembly of claim 7 having at least one tension adjusting component incorporated at an end of a tension wire.

14. An implant assembly to enhance bone elongation comprising:
   an extension implant having a first end, a second end, an external surface, an interior conduit, and a diameter, wherein the first end is adapted to be inserted into live bone;
   an enlarged implant having an interior conduit, wherein the interior conduit of the extension implant is in fluid communication with the interior conduit of the enlarged implant; and
   wherein the enlarged implant has a first end which comprises a seat adapted to receive the second end of the extension implant and a second end having a diameter that is larger than a diameter of the first end and larger than the diameter of the extension implant; an axial opening in the second end of the enlarged implant whereby the interior conduit is confining to prevent fluid from leaking outside of the interior conduit.

15. The implant assembly of claim 14 further comprising an annular space between the extension implant and a wall of the live bone to allow fluids to flow from the live bone to the external surface of the extension implant.

16. The implant assembly of claim 14 wherein the extension implant and the enlarged implant are comprised of calcium phosphate.

17. The implant assembly of claim 14 further comprising a plurality of grooves and openings on an exterior surface of the enlarged implant.

18. The implant assembly of claim 3 wherein an external cage assembly is used to supplement or replace the subcutaneous cage assembly.

* * * * *